United States Patent [19]

Strong

[11] 4,107,185

[45] Aug. 15, 1978

[54] 3-(3,4-EPOXY-4-METHYLCYCLOHEXYL)BUTYL ESTERS

[75] Inventor: Jerry G. Strong, Warren, N.J.

[73] Assignee: Mobil Oil Corporation, New York, N.Y.

[21] Appl. No.: 783,901

[22] Filed: Apr. 1, 1977

Related U.S. Application Data

[60] Division of Ser. No. 659,079, Feb. 18, 1976, Pat. No. 4,036,629, which is a continuation-in-part of Ser. No. 153,056, Jun. 14, 1971, abandoned.

[51] Int. Cl.$^2$ .......................................... C07D 303/44
[52] U.S. Cl. ............................................... 260/348.55
[58] Field of Search ................................... 260/348.55

[56] References Cited

U.S. PATENT DOCUMENTS

| | | | |
|---|---|---|---|
| 2,556,150 | 6/1951 | Wearn et al. | 560/124 |
| 3,590,053 | 6/1971 | Chase | 260/348.12 |

OTHER PUBLICATIONS

Chemical Abstracts, vol. 40 (1946) 14504.
Becco Chemical Division, Food Machinery and Chemical Corp. Station B Buffalo 7, New York, Bulletin #81, pp. 1-7.

*Primary Examiner*—Norma S. Milestone
*Attorney, Agent, or Firm*—Charles A. Huggett

[57] ABSTRACT

3-(3,4-Epoxy-4-methylcyclohexyl)butyl esters form a new class of compounds exhibiting fungicidal activity and plant growth regulant activity. In fungicide tests, the compounds of this invention prove effective against *Fusarium oxysporium, Pythium debaryanum, Rhizoctonia solani* and *Sclerotium rolfsii.* In herbicide tests, post-emergent application of the compounds of this invention provides plant growth regulant action, such as cotton defoliation and plant growth retardation activity.

1 Claim, No Drawings

3-(3,4-EPOXY-4-METHYLCYCLOHEXYL)BUTYL ESTERS

CROSS-REFERENCE TO RELATED APPLICATIONS

This application is a Division of copending application Ser. No. 659,079, filed Feb. 18, 1976, now U.S. Pat. No. 4,036,629 which was a continuation-in-part of application Ser. No. 153,056, filed June 14, 1971, now abandoned. It is related to Ser. No. 153,058, filed June 14, 1971, now U.S. Pat. No. 3,826,840, entitled 3-(4-METHYL-3-CYCLOHEXENYL)BUTYL ESTERS AND EPOXIDIZED DERIVATIVES THEREOF AS INSECT JUVENILE HORMONE MIMICKING COMPOUNDS AND INSECTICIDES.

BACKGROUND OF THE INVENTION

1. Field of the Invention

This invention is directed to the novel compounds 3-(3,4-epoxy-4-methylcyclohexyl)butyl esters and their use as fungicides and plant growth regulants.

2. Description of the Prior Art 3-(4-Methyl-3-cyclohexenyl) butanol, a compound useful in the synthesis of the compounds of this invention, is described in U.S. Pat. No. 2,556,150. The above patent discloses said butanol compound and its simple alkylcarboxylic acid esters, such as esters of acetic acid, propionic acid and butyric acid, as new compounds having desirable and persistent odors.

French Pat. No. 2,007,187 discloses certain specific derivatives of cyclohexene as insecticides.

SUMMARY OF THE INVENTION

This invention provides compounds having the formula:

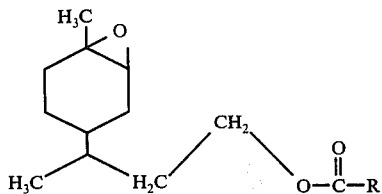

wherein R is an organic radical selected from the group consisting of phenyl, hydrogen, heterocyclic aryl, heterocyclic alkyl, cycloalkyl of 3-12 carbon atoms, alkyl of 1-12 carbon atoms, alkenyl of 2-12 carbon atoms, alkynyl of 2-12 carbon atoms, epoxyalkyl of 2-6 carbon atoms, aralkyl, diaralkyl and combinations of these as parts of the same radical, which radical may have substituted thereon one or more members selected from the group consisting of hydrogen, halogen (e.g., fluorine, chlorine and bromine), nitro, alkoxy of 1-carbon atoms, phenoxy, substituted phenoxy, haloalkyl of 1-4 carbon atoms, aryl, aroyl, acetyl, cyano, mercapto, alkylmercapto of 1-4 carbon atoms, hydroxy, carbalkoxy of 2-4 carbon atoms, carboxy, alkylamino of 1-4 carbon atoms, amide, alkyl of 1-6 carbon atoms, alkenyl of 2-6 carbon atoms, cycloalkyl of 3-6 carbon atoms, epoxyalkyl of 2-6 carbon atoms and combinations thereof; use as fungicides; use as plant growth regulants; fungicidally effective compositions containing at least one such compound and a carrier therefor; and effective plant growth regulant compositions containing at least one such compound and a carrier therefor.

DESCRIPTION OF SPECIFIC EMBODIMENTS

As will be noted from the above formula, the compounds of this invention are 3-(3,4-epoxy-4-methylcyclohexyl)-butyl esters. Mon-limiting examples of the compounds embodied for use in this invention include:

Acetic acid, 3-(3,4-epoxy-4-methylcyclohexyl)butyl ester;
Butyric acid, 3-(3,4-epoxy-4-methylcyclohexyl)butyl ester;
iso-Butyric acid, 3-(3,4-epoxy-4-methylcyclohexyl)butyl ester;
Pivalic acid, 3-(3,4-epoxy-4-methylcyclohexyl)butyl ester;
Cyclopropanecarboxylic acid, 3-(3,4-epoxy-4-methylcyclohexyl)butyl ester;
Cyclohexanecarboxylic acid, 3-(3,4-epoxy-4-methylcyclohexyl)butyl ester;
2-Chloroacetic acid, 3-(3,4-epoxy-4-methylcyclohexyl)butyl ester;
2,2-Dichloropropionic acid, 3-(3,4-epoxy-4-methylcyclohexyl)butyl ester;
2,2,3-Tribromobutyric acid, 3-(3,4-epoxy-4-methylcyclohexyl)butyl ester;
2-Nitropropinic acid, 3-(3,4-epoxy-4-methylcyclohexyl)butyl ester;
2-Methoxypropionic acid, 3-(3,4-epoxy-4-methylcyclohexyl)butyl ester;
2-Ethoxyacetic acid, 3-(3,4-epoxy-4-methylcyclohexyl)butyl ester;
2-iso-Propoxyacetic acid, 3-(3,4-epoxy-4-methylcyclohexyl)butyl ester;
2,3-Dimethoxybutyric acid, 3-(3,4-epoxy-4-methylcyclohexyl)butyl ester;
2-Phenoxypropionic acid, 3-(3,4-epoxy-4-methylcyclohexyl)butyl ester;
2-(2,4-Dichlorophenoxy)acetic acid, 3-(3,4-epoxy-4-methylcyclohexyl)butyl ester;
3-(2-Chloro-4-methylphenoxy)propionic acid, 3-(3,4-epoxy-4-methylcyclohexyl)butyl ester;
2-(2-Methyl-3,4-dichlorophenoxy)acetic acid, 3-(3,4-epoxy-4-methylcyclohexyl)butyl ester;
2-Phenylacetic acid, 3-(3,4-epoxy-4-methylcyclohexyl)butyl ester;
2,2-(p,p'-dichlorodiphenyl)acetic acid, 3-(3,4-epoxy-4-methylcyclohexyl)butyl ester;
2-Acetylpropionic acid, 3-(3,4-epoxy-4-methylcyclohexyl)butyl ester;
2-Cyanoacetic acid, 3-(3,4-epoxy-4-methylcyclohexyl)butyl ester;
2-Methylthiopropionic acid, 3-(3,4-epoxy-4-methylcyclohexyl)butyl ester;
2-Mercaptoacetic acid, 3-(3,4-epoxy-4-methylcyclohexyl)butyl ester;
2-Hydroxypropionic acid, 3-(3,4-epoxy-4-methylcyclohexyl)butyl ester;
2-Carboethoxypropionic acid, 3-(3,4-epoxy-4-methylcyclohexyl)butyl ester;
3-Carbomethoxybutyric acid, 3-(3,4-epoxy-4-methylcyclohexyl)butyl ester;
2-Dimethylaminobutyric acid, 3-(3,4-epoxy-4-methylcyclohexyl)butyl ester;
3-Dimethylacetamidopropionic acid, 3-(3,4-epoxy-4-methylcyclohexyl)butyl ester;
Crotonic acid, 3-(3,4-epoxy-4-methylcyclohexyl)butyl ester;
Cinnamic acid, 3-(3,4-epoxy-4-methylcyclohexyl)butyl ester;

3-Butenoic acid, 3-(3,4-epoxy-4-methylcyclohexyl)butyl ester;
3,3-Dimethyl-2-norbornaneacetic acid, 3-(3,4-epoxy-4-methylcyclohexyl)butyl ester;
5-Norbornene-2-carboxylic acid, 3-(3,4-epoxy-4-methylcyclohexyl)butyl ester;
3-Chlorocrotonic acid, 3-(3,4-epoxy-4-methylcyclohexyl)butyl ester;
Furoic acid, 3-(3,4-epoxy-4-methylcyclohexyl)butyl ester;
Tetrahydrofuroic acid, 3-(3,4-epoxy-4-methylcyclohexyl)butyl ester;
Benzoic acid, 3-(3,4-epoxy-4-methylcyclohexyl)butyl ester;
3,5-Dichlorobenzoic acid, 3-(3,4-epoxy-4-methylcyclohexyl)butyl ester;
Pthalic acid, 3-(3,4-epoxy-4-methylcyclohexyl)butyl ester;
Maleic acid, 3-(3,4-epoxy-4-methylcyclohexyl)butyl ester;
Tartaric acid, 3-(3,4-epoxy-4-methycyclohexyl)butyl ester;
2-Methoxy-3-chloropropionic acid, 3-(3,4-epoxy-4-methylcyclohexyl)butyl ester;
Oxalic acid, 3,4-epoxy-4-methylcyclohexyl)butyl ester;
2,3-Epoxypropionic acid, 3-(3,4-epoxy-4-methylcyclohexyl)butyl ester;
Formic acid, 3-(3,4-epoxy-4-methylcyclohexyl)butyl ester;
2,3-Epoxybutyric acid, 3-(3,4-epoxy-4-methylcyclohexyl)butyl ester; and
2,3-Epoxyisobutyric acid, 3-(3,4-epoxy-4-methylcyclohexyl)butyl ester;

The compounds of this invention are readily prepared using the following general Procedure I:

Procedure I 3-(3,4-Epoxy-4-methylcyclohexyl)butanol, prepared by the m-chloroperbenzoic acid epoxidation of 3-(4-methyl-3-cyclohexenyl) butanol, and an appropriate carboxylic acid halide are mixed in a suitable solvent, if desired, and with a suitable acid accepting agent, if desired. Non-limiting examples of solvents for use in this procedure include ethyl ether, chloroform, methylene chloride, benzene, toluene, hexane and heptane. Non-limiting examples of suitable acid accepting agents for use in this procedure include trialkylamines, triarylamines, pyridine and sodium carbonate. The resulting mixture is stirred and heated, if desired, for an appropriate time, and then washed with water, dried and evaporated to afford the desired product.

Various compounds of this invention can be prepared using an alternate procedure as described in the following general Procedure II:

Procedure II

Appropriate 3-(4-methyl-3-cyclohexenyl)butyl esters of carboxylic acids are mixed with a suitable epoxidizing agent in a suitable solvent. Non-limiting examples of suitable epoxidizing agents include m-chloroperbenzoic acid, perbenzoic acid, peracetic acid, perisophthalic acid, hydrogen peroxide and oxygen with suitable metal ion catalysts. Non-limiting examples of suitable solvents include ethyl ether, benzene toluene, chloroform, methylene chloride, hexane and heptane. The resulting mixture is stirred and cooled, if desired, for an appropriate time, and then filtered, washed with aqueous base, dried and evaporated to afford the desired product.

The following examples demonstrate the typical procedures. Examples 1-8 and 10-12 utilize above procedure II and Example 9 utilizes above procedure I.

EXAMPLE 1

SUCCINIC ACID, 3-(3,4-EPOXY-4-METHYLCYCLOHEXYL)BUTYL METHYL ESTER

An 8.2g (0.04 mole) portion of 85% m-chloroperbenzoic acid was added portionwise over 15 min. to a stirred, cooled (0°C.) solution of 11.3g (0.04 mole) of succinic acid, 3-(4-methyl-3-cyclohexenyl)butyl methyl ester in 250 ml of methylene chloride. The temperature rose to 10° C. during the addition and to ambient after the cooling bath was removed. The reaction mixture was stirred overnight. Sufficient 5% sodium hydroxide was added to dissolve the precipitated acid, and the organic layer was separated, washed with 5% sodium hydroxide and with brine, dried over magnesium sulfate and concentrated. Obtained was 10.6g of succinic acid, 3-(3,4-epoxy-4-methylcyclohexyl)butyl methyl ester as a clear, colorless liquid. The analytical determinations indicated that the product was pure and did not require further purification (See Table I).

EXAMPLE 2

CHLOROACETIC ACID, 3-(3,4-EPOXY-4-METHYLCYCLOHEXYL)BUTYL ESTER

The procedure of Example 1 was followed for the epoxidation of 7.9g (0.036 mole) of chloroacetic acid, 3-(4-methyl-3-cyclohexenyl)butyl ester using 7.4g (0.036 mole) of 85% m-chloroperbenzoic acid on 120 ml of methylene chloride. Obtained was 7.9g of pure chloroacetic acid, 3-(3,4-epoxy-4-methylcyclohexyl)butyl ester as a clear, colorless liquid. (See Table I).

EXAMPLE 3

CYCLOPROPANE CARBOXYLIC ACID, 3-(3,4-EPOXY-4-METHYLCYCLOHEXYL)BUTYL ESTER

The procedure of Example 1 was followed for the epoxidation of 4.7g (0.02 mole) of cyclopropanecarboxylic acid, 3-(4-methyl-3-cyclohexenyl)butyl ester using 4.2g (0.02 mole) of 85% m-chloroperbenzoic acid in 150 ml of methylene chloride. Obtained was 4.1g of cyclopropanecarboxylic acid, 3-(3,4-epoxy-4-methylcyclohexyl)butyl ester as a celar, colorless liquid (See Table I).

EXAMPLE 4

METHOXYACETIC ACID, 3-(3,4-EPOXY-4-METHYLCYLOHEXYL)BUTYL ESTER

The procedure of Example I was followed for the epoxidation of 4.8g (0.02 mole) of methoxyacetic acid, 3-(4-methyl-3-cyclohexenyl)butyl ester using 4.1g (0.02 mole) of 85% m-chloroperbenzoic acid in 150 ml of methylene chloride. Obtained was 4.3g of pure methoxyacetic acid, 3-(3,4-epoxy-4-methylcyclohexyl)butyl ester as a clear, colorless liquid. (See Table I).

EXAMPLE 5

2-PHENOXYBUTYRIC ACID, 3-(3,4-EPOXY-4-METHYLCYCLOHEXYL)BUTYL ESTER

The procedure of Example 1 was followed for the epoxidation of 7.6g (0.023 mole) of 2-phenoxybutyric acid, 3-(4-methyl-3-cyclohexenyl)butyl ester using 4.8g (0.023 mole) of 85% m-chloroperbenzoic acid in 120 ml of methylene chloride. Obtained was 5.6g of pure 2-phenoxybutyric acid, 3-(3,4-epoxy-4-methylcyclohexyl)butyl ester as a clear, colorless liquid. (See Table I).

EXAMPLE 6

ETHOXYACETIC ACID, 3-(3,4-EPOXY-4-METHYLCYCLOHEXYL)BUTYL ESTER

The procedure of Example 1 was followed for the epoxidation of 5.0g (0.02 mole) of ethoxyacetic acid, 3-(4-methyl-3-cyclohexenyl)butyl ester using 4.1g (0.02 mole) of 85% m-chloroperbenzoic acid in 130 ml of methylene chloride. Obtained was 5.2g of pure ethoxyacetic acid, 3-(3,4-epoxy-4-methylcyclohexyl)butyl ester as a clear, colorless liquid. (See Table I).

EXAMPLE 7

SUCCINIC ACID, 3-(3,4-EPOXY-4-METHYLCYCLOHEXYL)BUTYL ESTER

The procedure of Example 1 was followed for the epoxidation of 7.0g (0.03 mole) of succinic acid, 3-(4-methyl-3-cyclohexenyl)butyl ester using 6.0g (0.03 mole) of 85% m-chloroperbenzoic acid in 120 ml of chloroform, except that following an overnight stir, the reaction mixture was cooled to 0°c. and the separated m-chlorobenzoic acid was filtered. The filtrate was diluted with ether and washed with water, dried over magnesium sulfate and concentrated. Obtained was 4.1g of pure succinic acid, 3-(3,4-epoxy-4-methylcyclohexyl)butyl ester as a clear, viscous oil (See Table I).

EXAMPLE 8

PIVALIC ACID, 3-(3,4-EPOXY-4-methylcyclohexyl)BUTYL ESTER

The procedure of Example 1 was followed for the epoxidation of 4.0g (0.016 mole) of pivalic acid, 3-(4-methyl-3-cyclohexenyl)butyl ester using 4.2g (0.02 mole) of 85% m-chloroperbenzoic acid in 150 ml of methylene chloride. Obtained was 4.2g of pure pivalic acid, 3-(3,4-epoxy-4-methylcyclohexyl)butyl ester as a clear, colorless liquid. (See Table I).

EXAMPLE 9 trans-CHRYSANTHEMUMIC ACID, 3-(3,4-EPOXY-4-METHYLCYCLOHEXYL)BUTYL ESTER (1) 3-(3,4-Epoxy-4-methylcyclohexyl)butanol The procedure of Example 1 was followed for the epoxidation of 16.8g (0.1 mole) of 3-(4-methyl-3-cyclohexenyl)butanol using 22.2g (0.11 mole) of 85% m-chloroperbenozic acid, except that 23.4g (0.22 mole) of sodium carbonate was added to the reaction flask before the addition of peracid. A 250 ml portion of methylene chloride served as solvent. Following an overnight stir at ambient temperature, 200 ml of water was aded and the organic layer was separated, washed with 5% sodium hydroxide and with brine, dried over magnesium sulfate and concentrated. Obtained was 18.6g of 3-(3,4-epoxy-4-methylcyclohexyl)butanol as a clear, colorless liquid, which was used in the next step without further purification.

(b) trans-Chrysanthemumic acid, 3-(3,4-epoxy-4-methylcyclohexyl)butyl ester

A 5.6g (0.03 mole) portion of trans-chrysanthemumic acid chloride in 15 ml of ethyl ether was added dropwise to a stirred solution of 5.5g (0.03 mole) of the product compound of Example 9a and 6.1g (0.06 mole) of triethylamine in 150 ml of ehtyl ether. The reaction mixture was stirred overnight at ambient before sufficient water was added to dissolve the separated salts. The organic layer was separated, washed with 5% sodium hydroxide and with brine, dried over magnesium sulfate and concentrated. Obtained was 9.2g of pure trans-chrysanthemumic acid, 3-(3,4-epoxy-4-methylcyclohexyl)butyl ester as a clear, colorless liquid (See Table I).

EXAMPLE 10

ACETIC ACID, 3-(3,4-EPOXY-4-METHYLCYCLOHEXYL)BUTYL ESTER

The procedure of Example 1 was followed for the epoxidation of 4.2g (0.02mole) of acetic acid, 3-(4-methyl-3-cyclohexenyl)butyl ester using 4.1g (0.02 mole) of 85% m-chloroperbenzoic acid in 150 ml of methylene chloride. Obtained was 4.1g of pure acetic acid, 3-(3,4-epoxy-4-methylcyclohexyl)butyl ester as a clear, colorless liquid. (See Table I).

EXAMPLE 11

FUROIC ACID, 3-(3,4-EPOXY-4-METHYLCYCLOHEXYL)BUTYL ESTER

The procedure of Example 1 was followed for the epoxidation of 5.2g (0.02 mole) of furoic acid, 3-(4-methyl-3-cyclohexenyl)butyl ester using 4.2g (0.02 mole) of 85% m-chloroperbenzoic acid in 150 ml of methylene chloride. Obtained following distillation was 3.7g of pure furoic acid, 3-(3,4-epoxy-4-methylcyclohexyl)butyl ester as a clear, colorless liquid with a boiling point of 156°–161°C. (0.10mm). (See Table I).

EXAMPLE 12

TRICHLOROACETIC ACID, 3-(3,4-EPOXY-4-METHYLCYCLOHEXYL)BUTYL ESTER

The procedure of Example 1 was followed for the epoxidation of 6.3g (0.02 mole) of trichloroacetic acid, 3-(4-methyl-3-cyclohexenyl)butyl ester using 4.2g (0.02 mole) of 85% m-chloroperbenzoic acid in 150 ml of methylene chloride. Obtained was 5.1g of pure trichloroacetic acid, 3-(3,4-epoxy-4-methylcyclohexyl)butyl ester as a clear, colorless liquid (See Table I).

TABLE I

INFRARED, NUCLEAR MAGNETIC RESONANCE AND MASS SPECTRA OF THE COMPOUNDS OF EXAMPLES 1-12

| COMPOUND OF EXAMPLE | IR [γ(max) microns] film | NMR [δ in ppm (nH, pattern)] | MS (parent ion) |
|---|---|---|---|
| 1 | 3.5(s), 5.8(s), 7.0 (m), 8.7(s), 11.8 (m). | 4.05(2H, t), 3.66 (3H, s), 2.99 and 2.91 (1H, d and s), 2.60 (4H, s). | 290 |
| 2 | 3.5(s), 5.8(s), 6.9 (m), 8.5(s), 11.9(m). | 4.15 (2H, t), 4.0 (2H, s), 2.96 and 2.89 (1H, d and s). | 260 |
| 3 | 3.5(s), 5.9(s), 6.9 (m), 8.6(s), 11.8(m). | 4.11(2H, t), 3.05 and 3.0(1H, d and s), 0.96 (5H, m). | 252 |
| 4 | 3.4(s), 5.8(s), 6.9 (m), 8.4(s), 8.8(s), 11.8(m). | 4.11(2H, t), 3.97(2H, s), 3.37 (3H, s), 2.95 and 2.89(1H, d and s). | 256 |
| 5 | 3.5(s), 5.8(s), 6.8 (s), 8.2(s), 8.4(s), 11.8(m). | 7.27 to 6.72(5H, m); 4.50(1H, t), 4.08(2H, t), 2.92 and 2.82(1H, d and s). | 346 |
| 6 | 3.5(s), 5.8(s), 7.0 (m), 8.4(s), 8.9(s), 11.8(m). | 4.12(2H, t), 4.0(2H, s), 3.57(2H,q), 2.97 and 2.90 (1H, d and s). | 270 |
| 7 | 3.2(m), 3.5(s), 5.8 (s), 8.6(s), 11.8(m) | 4.07(2H, t), 2.58(4H, s), 2.98 and 2.92 (1H, d and s). | — |
| 8 | 3.5(s), 5.8(s), 6.9 (s), 8.7(s), 11.8(m) | 3.99(2H, t), 2.93 and 2.86(1H, d and s). | 268 |
| 9 | 3.5(s), 5.8(s), 6.9 (s), 8.6(s), 11.7(m) | 4.84(1H, d), 4.01(2H, t), 2.94 and 2.88(1H, d and s). | 334 |
| 10 | 3.4(s), 5.8(s), 6.9 (m), 8.2(s), 9.5(m), 11.8(m). | 4.01(2H, t), 2.95 and 2.88 (1H, d and s), 1.99 (3H, s). | 226 |
| 11 | 3.5(s), 5.9(s), 6.8 (m), 7.8(s), 8.9(s), 11.8(m). | 7.54(1H, m), 7.11(1H, d), 6.43 (1H, q), 4.27 (2H, t), 2.98 and 2.91 (1H, d and s). | 278 |
| 12 | 3.5(s), 5.7(s), 6.9 (m), 8.1(s), 10.2(m), 12.1(s). | 4.32(2H, m), 2.98 and 2.91 (1H, d and s). | 328 |

In illustration of the utility of this invention, the compounds of the examples were subjected to tests for fungicidal activity and plant growth regulant activity according to the following test descriptions. The results of said tests are set forth in Tables II, III and IV following the descriptions.

FUNGICIDE TESTING METHOD

Four representative soil fungi, *Fusarium oxysporium, Pythium debaryanum, Rhizoctonia solani* and *Sclerotium rolfsii*, are maintained on potato dextrose agar in 20 × 150 mm. test tubes. Inoculum for the test is increased in a 1000 ml. Erlenmeyer flask on a one-fourth corn meal three-fourths sand mixture (by volume). The medium is saturated with water and sterilized by autoclaving at 15 lbs. pressure for 20 minutes on two successive days. The medium is inoculated by transferring, aseptically, a small portion of mycelium from the test tube cultures 14 days prior to using for inoculum.

An inoculated medium for each of the four soil organisms is prepared as follows: A 14-day old 1000 ml. flask of the corn meal-sand inoculum is used to inoculate 20 10-oz. cups of sterile soil by blending the inoculum and sterile soil for 10 minutes in the cement mixer.

The inoculated medium is then placed in 10 oz. wax treated cold drink cups (20 cups of each organism) and treated as follows: 150 mg quantity of each candidate fungicide is weighed on the analytical balance and formulated using 10 ml. of acetone and 190 ml. of H$_2$O. A 50 ml. quantity of each chemical formulation is used to drench 1 cup inoculated with each of the four fungal organisms. Immediately after the cups are drenched, they are placed in polyethylene bags (1 cup per bag) and held at 70° F. for 14 days.

After 10 days, each cup is examined for the presence of fungal growth and each compound rated for per cent inhibition of fungal growth.

PLANT GROWTH REGULANT TESTING METHOD

The test species propagated for testing are cotton and bean.

Each specie is planted individually in 3 inch plastic pots containing potting soil. Four seeds each of the cotton and bean are seeded to a depth equal to the diameter of the seed. Immediately after planting, all pots are watered by sub-irrigation in greenhouse trays.

Planting dates of the cotton and bean species are varied so that each will reach the desired stage of development simultaneously. The proper stage of development for treatment of the cotton species is when the first true leaf is one inch in length and the cotyledons are expanded. The proper stage for the bean species is when the primary leaves are expanded and the growing point is at the primary leaf node.

Spray applications of test compounds are made in a hood containing a movable belt and fixed spray nozzle. Treatments are moved to the greenhouse after spraying. Watering during the observation period is accomplished only by sub-irrigation.

Compounds are screened at rates of application equivalent to 16 and 8 pounds actual per acre in a spray volume of 38 gallons per acre. Spray hood constants required to deliver the above volume are as follows:

| | |
|---|---|
| Belt speed: | 2 mph |
| Air Pressure: | adjusted to provide 38 gpa delivery |

-continued

| Nozzle Tip: | 8003E (provides uniform cross-section flat spray) |

Formulations for spray applications (as used in the compositions for which data are set forth in the Table III hereinafter provided) are prepared in 50 ml. volumes with the following components:

| | SIXTEEN POUNDS PER ACRE RATE |
|---|---|
| 1. | 2.48 grams compound |
| 2. | 49 ml. acetone as solvent |
| 3. | 1 ml. xylene-Atlox 3414 (surface-active emulsifier) |

| | EIGHT POUNDS PER ACRE RATE |
|---|---|
| 1. | 1.24 grams compound |
| 2. | 49 ml. acetone as solvent |
| 3. | 1 ml. xylene-Atlox 3414 (surface-active emulsifier |

Compounds which are not available in sufficient quantity for machine spraying are applied by hand with a DeVilbiss atomizer.

Two weeks after treatment, an evaluation is made as to plant defoliation or growth retardation.

U.S. Pat. No. 2,556,150, 3-(4-methyl-3-cyclohexenyl)-butyl acetate.

The test species (bean) was propogated as per below. A standard Lanolin Paste Method of testing was used. The procedure of which is described below and in U.S.-D.A. Agriculture Handbook No. 336, pages 8 and 56-57. (United States Department of Agriculture).

METHOD OF TREATMENT

Three or four seeds of the bean species to be tested were planted per pot. When the plants were ready for treatment, i.e. when the primary leaves had expanded and the growing point was at the primary leaf mode, the seedlings were thinned to one plant per pot. Four replicate (duplicate) plants were used for each treatment.

Treatment was made by placing a band of lanolin paste 3-6 mm wide around the first internode midway between the first and second nodes of each bean plant. The lanolin paste formulation contained:
12.5 mg test material
500 mg Tween 20 (Commercial Surfactant)
2 grams lanolin (anhydrous)

METHOD OF RECORDING RESULTS

One week after treatment stem measurements were made from the node immediately above the treated section of the stem and determining the distance from this point to tip of the terminal bud. All of the plants in

TABLE II

FUNGICIDAL ACTIVITY* OF THE COMPOUNDS OF THIS INVENTION

| COMPOUND OF EXAMPLE | CONCENTRATION OF APPLICATION, PPM (PARTS PER MILLION) | ORGANISM CONTACTED FUSARIUM OXYSPORIUM | PYTHIUM DEBARYA-NUM | RHIZOCTONIA SOLANI | SCLEROTIUM ROLFSII |
|---|---|---|---|---|---|
| 1 | 25 | 30 | 30 | 70 | 70 |
| 2 | 50 | 90 | 90 | 70 | 70 |
| 3 | 50 | 60 | 10 | 60 | 60 |
| 4 | 50 | 60 | 10 | 60 | 60 |
| 5 | 25 | 30 | 30 | 30 | 30 |
| 6 | 50 | 30 | 60 | 40 | 40 |
| 7 | 25 | 30 | 30 | 10 | 10 |
| 8 | 25 | 100 | 40 | 90 | 90 |
| 9 | 25 | 20 | 20 | 80 | 80 |
| 10 | 50 | 50 | 10 | 10 | 10 |
| 11 | 25 | 80 | 10 | 50 | 50 |
| 12 | 25 | 70 | 40 | 70 | 70 |

*Fungicidal Activity is measured in percent effectiveness

TABLE III

PLANT GROWTH REGULANT ACTIVITY OF THE COMPOUNDS OF THIS INVENTION

| COMPOUND OF EXAMPLE | CONCENTRATION OF APPLICATION, lbs/acre | PLANT SPECIES | RESULTS |
|---|---|---|---|
| 2 | 16 | Cotton | 100% defoiliation of the true leaves and cotyledonary leaves leaving a healthy stem, i.e. mechanical harvesting aid. |
| 4 | 8 | Bean | Estimated 35 % retardation of the main stems leaving a shorter, sturdier plant. |
| 5 | 8 | Bean | Proliferation of the terminal buds affording a bushier, fuller plant. |
| 8 | 8 | Bean | Kill of the new terminal buds; an effect similar to that of a contact tobacco sucker control agent. |

Table IV below is a direct comparison of the plant growth regulant activity of a compound in accordance with the invention embodied herein namely the compound of Example 4, methoxyacetic acid, 3-(3,4-epoxy-4-methylcyclohexyl)butyl ester otherwise designated as 3-(3-4-epoxy-4-methylcyclohexyl)butyl methoxyacetate and a prior art compound, the compound of Example 5, each of the four groups (see Table IV) were similary measured. Percent growth inhibition or stimulation was determined from the average length (mm) of each treatment in the following formula:

$$\frac{\text{Untreated control minus treated}}{\text{Untreated control}} \times 100 = \% \text{ inhibition (plus value) or stimulation (minus value)}$$

Groups I and II respectively contained the test material[1], i.e., a compound according to Example 5 of U.S. Pat. No. 2,556,150 or Example 4 of this application. The data indicate the growth increase in height in centimeters for each plant over an eight-day period following treatment. Also included is the average growth increase for each treated series and a percent growth inhibition for each compound as compared to the lanolin paste blank (Group II) and an untreated check (Group IV).

[1] At application rates of 0.5 wt. %.

TABLE IV
COMPARISON OF PLANT GROWTH REGULANT EFFECTS OF THE COMPOUND OF EXAMPLE 5 OF U.S. Pat. No. 2,556,150 AND THE COMPOUND OF EXAMPLE 4 OF THIS APPLICATION AT APPLICATION RATES OF 0.5 WEIGHT % OF TEST COMPOUND

|  |  | COMPOUND | | | |
|---|---|---|---|---|---|
|  | SPECIMEN | EXAMPLE 5 GROUP I | EXAMPLE 4 GROUP II | PASTE BLANK GROUP III | UNTREATED GROUP IV |
| STEM GROWTH INCREMENT | 1 | 3.7 | 1.5 | 2.9 | 3.0 |
|  | 2 | 5.0 | 4.8 | 7.0 | 5.9 |
|  | 3 | 8.7 | 4.8 | 7.4 | 9.3 |
|  | 4 | 4.3 | 4.0 | 5.2 | 4.2 |
|  | 5 | 6.3 | 3.8 | 8.7 | 11.7 |
|  | 6 | 7.7 | 3.8 | 4.1 | 3.8 |
|  | 7 | 3.5 | 3.5 | 3.6 | 3.5 |
|  | 8 | 7.6 | 5.1 | 7.2 | 6.3 |
| ARITHMETIC MEAN (AVERAGE) % INHIBITION |  | 5.9 | 3.9 | 5.8 | 6.0 |
| Compared Against PASTE BLANK (III) |  | −2% | 33% |  |  |
| Compared against UNTREATED BLANK (IV) |  | 2% | 35% |  |  |

The data of Table IV clearly demonstrates that the compound of Example 5, 3-(4-methyl-3-cyclohexenyl)-butyl acetate, of U.S. Pat. No. 2,556,150 exerts little if any growth regulant effects on beans at 0.5% concentration in the standard lanolin paste test whereas a compound in accordance with this invention, the compound of Example 4, methoxyacetic acid (3,4-epoxy-4-methyl-cyclohexyl)butyl ester exerts a highly significant degree of retardation on bean plant growth approximately 31–33%.

From the data in Tables II, III, and IV it will be noted that the 3-(3,4-eopxy-4-methylcyclohexyl)butyl esters of the present invention have a broad range of fungicidal activity and exhibit plant growth regulant and cotton defoliation activity. They are effective in the fungicide tests against Fusarium oxysporium, a fungus representing a huge genus of plant disease organisms; Pythium debaryanum, an important disease which causes decay, damping off and storage rot of cotton and many other plants; Rhizoctonia solani and Sclerotium folfsii, complex disease organisms which cause damping off of practically all crops. The compounds of this invention also show 100% defoliation of the true leaves and cotyledonary leaves of cotton plants, thus providing an aid to mechanical harvesting. The compounds also show stem retardation and bud proliferation of bean plants, thus providing a shorter, sturdier, bushier plant which is more resistant to weather damage. Furthermore, in a direct side by side plant growth regulant comparison study with a prior art compound (Example 5 of U.S. Pat. No. 2,556,150) the compound of Example 4 of the present invention retarded the stem growth of the test specie (bean plants) by approximately one-third; the prior art compound had a negligible effect upon stem growth.

The compounds of this invention, in exhibiting considerable fungicidal activity and plant growth regulant activity, are disclosed for use in various ways to achieve such utility. They can be applied per se, as solids or in vaporized form, but are preferably applied as the toxic components in fungicidal and plant growth regulant compositions of the compound and a carrier. The compositions can be applied as dusts, as liquid sprays or as gas-propelled sprays and can contain, in addition to a carrier, additives such as emulsifying agents, wetting agents, binding agents, gases compressed to the liquid state, odorants, stabilizers and the like. A wide variety of liquid and solid carriers can be used in the fungicidal and plant growth regulant compositions. Non-limiting examples of liquid carriers include water; organic solvents such as alcohols, ketones, amides, and esters; mineral oils such as kerosene, light oils, and medium oils; and vegetable oils such as cottonseed oil. Non-limiting examples of solid carriers include talc, bentonite, diatomaceous earth, pyrophyllite, fuller's earth, gypsum, flours derived from cottonseeds and nut shells, and various natural and synthetic clays having a pH not exceeding about 9.5.

The amount of the compounds of this invention utilized in fungicidal and plant growth regulant compositions will vary rather widely. It depends to some extend upon the type of composition in which the material is being used, the nature of the condition to be controlled, and the method of application (i.e., spraying, dusting, etc.). In the ultimate fungicidal and plant growth regulant composition, as applied in the field, active compound concentrations as low as 0.0001 weight percent of the total composition can be used. In general compositions, as applied, containing about 0.05 weight percent active compound in either liquid or solid carrier give excellent results. In some cases, however, stronger dosages up to about 10 weight percent may be required.

In practice, fungicidal and plant growth regulant compositions are usually prepared in the form of concentrates, which are diluted in the field to the concentration desired for application. For example, the concentrate can be a wettable powder containing large amounts of a compound of this invention, a carrier (e.g., attapulgite or other clay), and wetting and dispersing agents. Such a powder can be diluted prior to application, by dispersing it in water to obtain a sprayable suspension containing the concentration of active compound desired for application. Other concentrates can be solutions that can be later diluted, e.g., with kerosene. Thus, it is within the contemplation of this invention to provide fungicidal and plant growth regulant compositions containing up to about 80 percent, by weight of the composition, of an active compound of this invention.

Accordingly, depending upon whether it is ready for application or it is in concentrated form the contemplated fungicidal and plant growth regulant compositions contain between about 0.0001 percent and about 80 percent, by weight of the composition of an active compound of this invention, and a carrier, liquid or solid, as defined hereinbefore.

Although the present invention has been described with preferred embodiments, it is to be understood that modifications and variations may be resorted to without departing from the spirit and scope of this invention, as those skilled in the art will readily understand.

What is claimed is:

1. A compound of the formula:

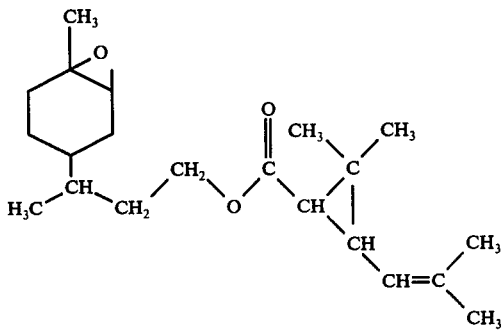

which is named:
3-(3,4-Epoxy-4-methylcyclohexyl)butyl 2,2-dimethyl-3-(2-methylpropenyl)cyclopropanecarboxylate.

* * * * *